US00PP11226P

United States Patent [19]

Turner

[11] Patent Number: Plant 11,226

[45] Date of Patent: Feb. 15, 2000

[54] APPLE TREE 'LOCHBUIE RED BRAEBURN'

[76] Inventor: William Turner, Lochbuie Orchard, 453 Main Road North, Belfast Chch 8005, New Zealand

[21] Appl. No.: 08/786,166

[22] Filed: Jan. 21, 1997

[51] Int. Cl.[7] ..... A01H 5/00

[52] U.S. Cl. ..... Plt./161

[58] Field of Search ..... Plt./34.1, 161

[56] References Cited

U.S. PATENT DOCUMENTS

P.P. 7,526 5/1991 Hill et al. ..... Plt./34.1

OTHER PUBLICATIONS

GTITM UPOV–ROM Citation NZ PBR APP048 for 'Lochbuie' filed Jun. 24, 1986, Jul. 1986.

*Primary Examiner*—Howard J. Locker
*Attorney, Agent, or Firm*—Quarles & Brady LLP

[57] ABSTRACT

The new and distinct variety of apple tree is a mutation of Braeburn (an unpatented New Zealand variety). The new variety is characterized by very attractive highly colored red fruit. The color is in the form of a red blush rather than the stripe and fleck of standard Braeburn. The new variety has been named 'Lochbuie Red Braeburn'.

2 Drawing Sheets

BACKGROUND SUMMARY

The subject of this application is a sport of the Braeburn Apple variety, *Malus domestica*. The Braeburn apple variety is a popular commercial product. Its commercial attractiveness has developed such that it now holds its own market class with many orchards planting the Braeburn tree. Often times, the wide planting of a popular tree variety amongst orchards results in a number of attractive color sports with one or more enhanced features, such as differing harvest dates or different over colors possessing a higher eye appeal.

The Lochbuie Red Braeburn is such a sport, and has been thoroughly compared to its parent and known and commercially available sibling varieties. Comparisons were made with the varieties Braeburn, Hidala (U.S. Plant Pat. No. 7,526), Mariri Red (U.S. Plant patent application Ser. No. 08/980,181) and Joburn (U.S. Plant patent application Ser. No. 08/979,898) on the basis of the descriptions and recorded differences as recited by the New Zealand Plant Variety Rights Office. The Lochbuie Red Braeburn variety has its own distinct features such that its commercial attractiveness will continue the success of the Braeburn Apple group.

SUMMARY OF THE INVENTION

The mutation was discovered in 1985 on an apple tree that had been grafted over to the Braeburn variety on the owner's orchard near Christchurch, New Zealand as a single branch which was producing apples that were distinctly redder than what was expected for the Braeburn variety. Graftwood from this branch taken in 1987 was used to produce 27 further trees on MM106 rootstock. When these trees came into fruiting the highly colored characteristic of fruit was contained in all of the 27 trees, showing that the mutation was stable. The very attractive fruit that was produced by mutation encouraged the owner to proceed with the development of the variety so that the benefits of an improved Braeburn sport could be enjoyed by the entire industry.

Since the discovery of the mutation 5 generations of asexual propagation show that the unique combination of characteristics and distinctive color come true to form and are established and transmitted through succeeding generations.

DETAILED DESCRIPTION OF THE DISCLOSURE

The distinctive characteristics of the Lochbuie Red Braeburn variety and the comparative differences with the prior varieties mentioned above are described as follows. The fruit of the Lochbuie Red Braeburn is a late harvesting fruit with a premium harvest maturity one week later than that of Braeburn and Hidala, and two weeks later than Joburn and Mariri Red (Table 1). The Braeburn and Hidala fruits ripen around the 20th of March in Hawkes Bay, New Zealand. At this time, the Lochbuie Red Braeburn fruit is still starchy to taste, while the typical coloration has not yet developed. It is not until the following week that the Lochbuie Red Braeburn fruit develops its colorful appearance and is ready for harvesting.

Figure 3:
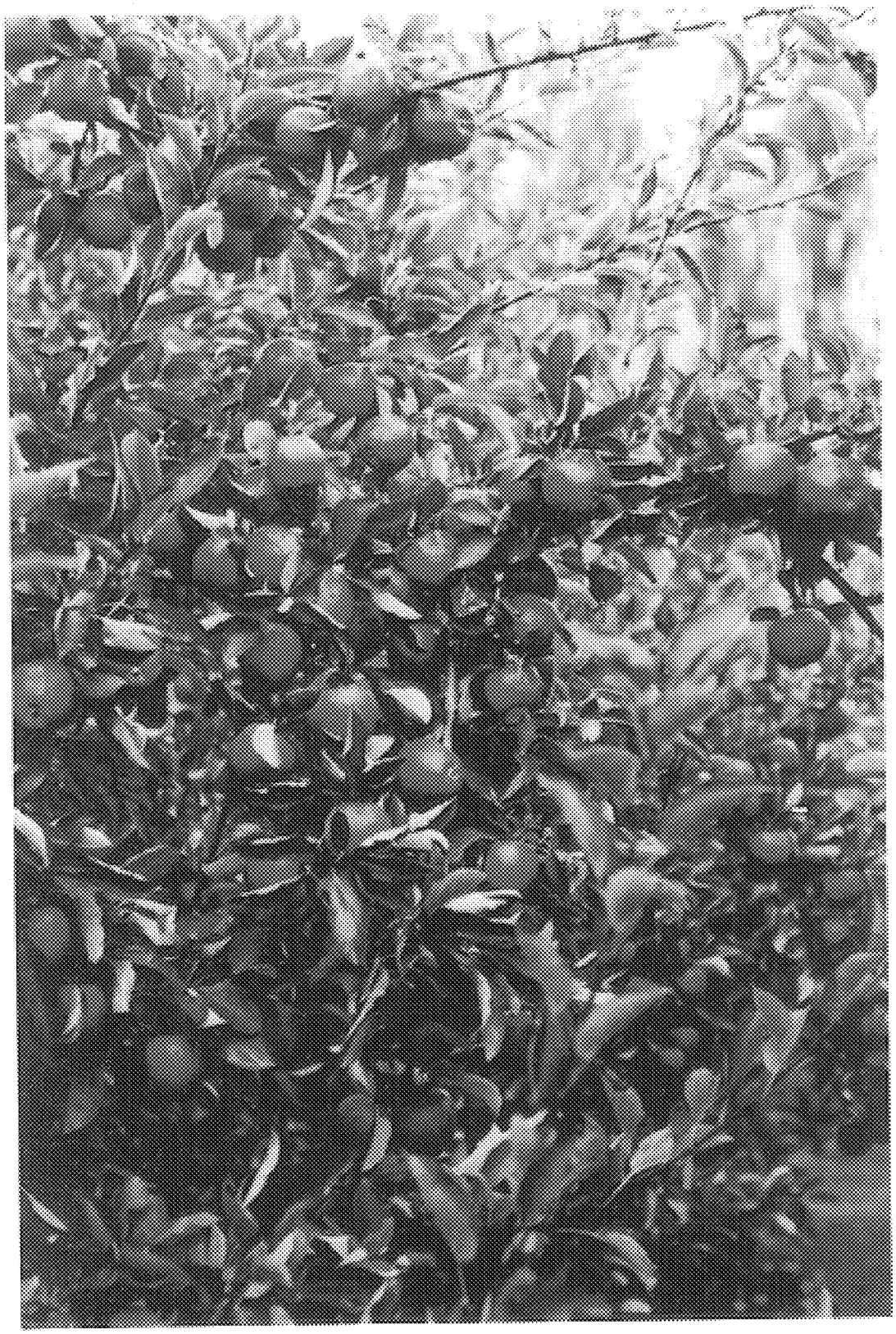
FIG. 3 shows a crop of Lochbuie Red Braeburn fruit on the tree.

At harvest, the distinct coverage of red colored apples throughout the Lochbuie Red Braeburn tree allows the fruit to be harvested in only two picks. This is because Lochbuie Red Braeburn has a more consistent coverage of red color apples throughout the tree as compared to Hidala and Braeburn varieties (FIG. 3). The Hidala and Braeburn varieties lack such a consistency and normally require 3–4 picks for a full harvest. Additionally, the increased coloration throughout the tree results in higher packouts of highly colored fruits as compared to Braeburn and Hidala.

Figure 1:
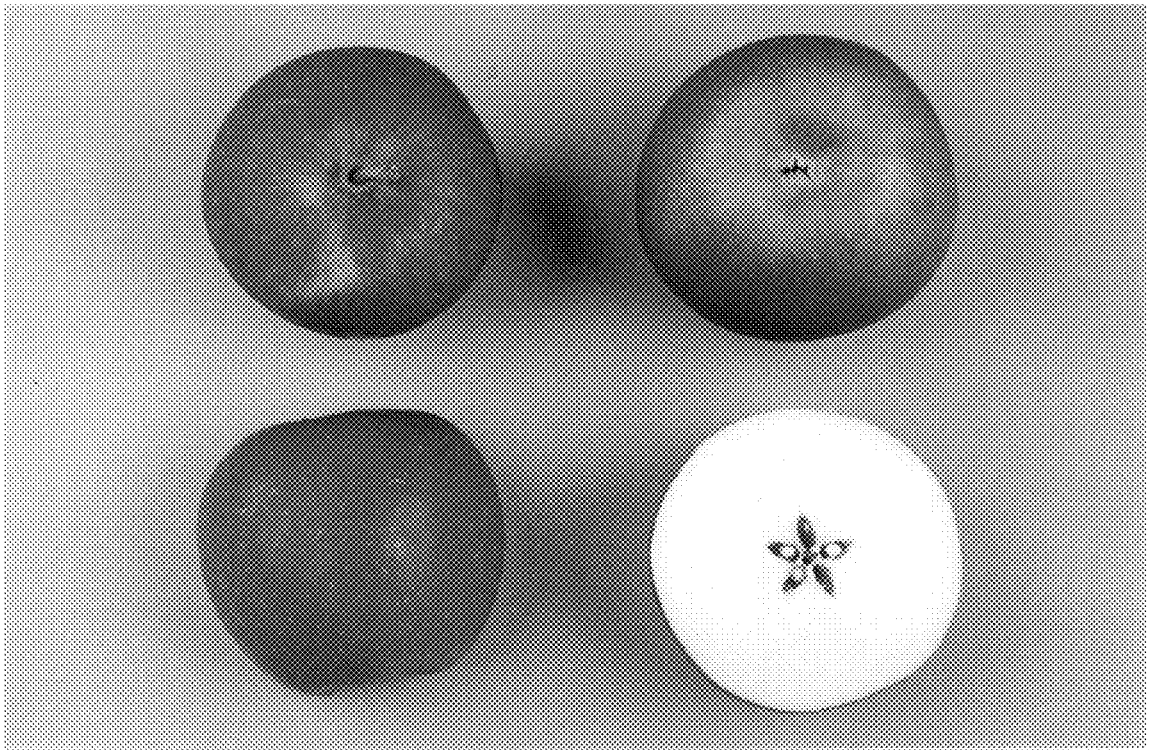
FIG. 1 shows the almost complete red coloration of 'Lochbuie Red Braeburn' from the stem-end, side-view and calyx-end, as well as a cross-sectional view.
Figure 2:
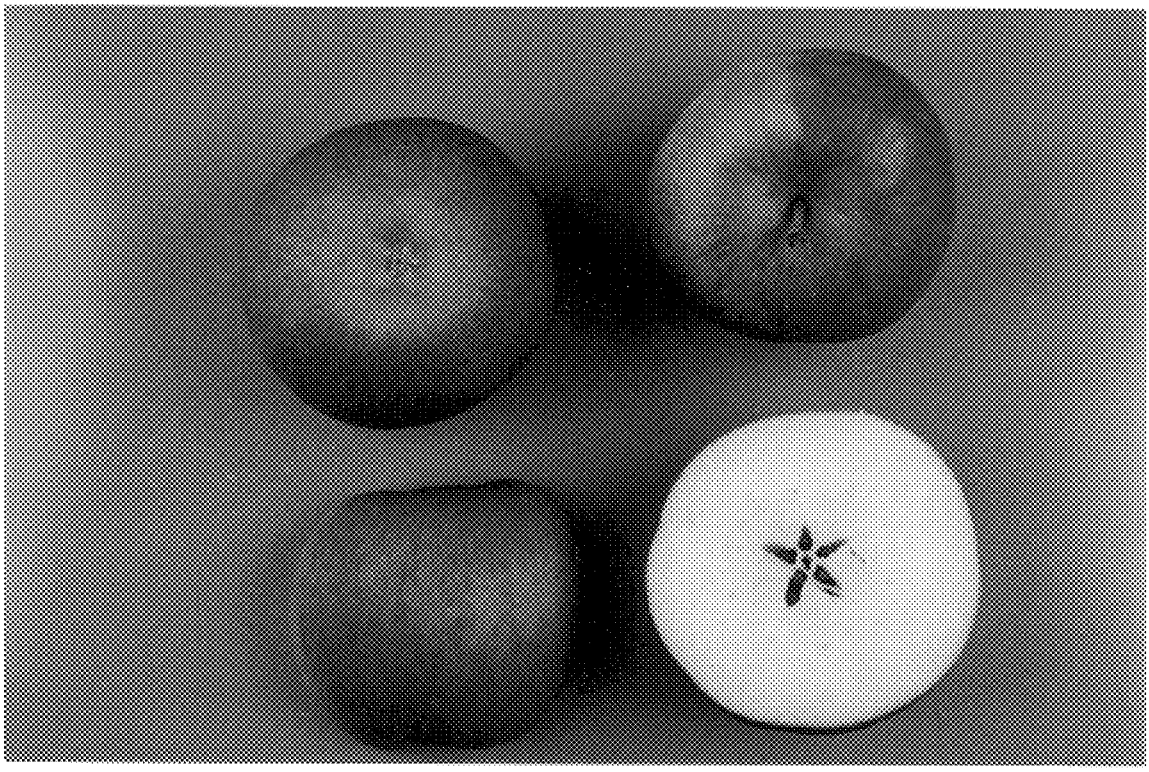
FIG. 2 shows the standard Braeburn from the stem-end, side-view and calyx-end, as well as a cross-sectional view.

The Lochbuie Red Braeburn fruit has a distinctive appearance. The fruit has a much higher red color coverage when compared to the Braeburn and Hidala varieties. Lochbuie Red Braeburn has an 80–90 percent red color coverage, whereas the Hidala and Braeburn fruits have a smaller amount of color coverage. Specifically, the Hidala fruit has a 50–70 percent coloration at harvest and the Braeburn has a 40–50 percent coloration at harvest. As shown in FIG. 1, the color pattern of Lochbuie Red Braeburn consists of a bright red blush and block with some indistinct striping visible on surfaces not exposed to the sun. This varies from the Hidala and Braeburn varieties where a distinct bold stripe and fleck dominates the color pattern (FIG. 2). As compared to the Joburn variety, the Lochbuie Red Braeburn fruit lacks the bold red stripes over a lighter red blush that is typical of Joburn. The Joburn fruit is 100 percent covered in stripes and blush whereas the Lochbuie Red Braeburn fruit maintains a 10–20 percent yellow background throughout its development. Although not distinctive using color charts, the over color of Lochbuie Red Braeburn fruit appears a lighter, brighter red than the coloration of Joburn. When compared to the Mariri Red variety, the Mariri Red over color is significantly darker (R.H.S.C.C. 187B) than that of Lochbuie Red Braeburn (R.H.S.C.C. 185A). The over color of the Mariri Red normally covers the fruit completely compared to the incomplete coverage that is evident in Lochbuie Red Braeburn.

TABLE 1

Comparison of Lochbuie Red Braeburn, Hidala, Joburn and Mariri Red

| | Lochbuie Red Braeburn | Hidala | Joburn | Mariri Red |
|---|---|---|---|---|
| Dormant One Year Old Shoot | | | | |
| Pubescence | present | absent | strong | strong |
| Leaf Pubescence | medium | weak | strong | strong |
| Fruit | | | | |
| Symmetry | asymmetric | symmetric | asymmetric | asymmetric |
| Ribbing | absent | absent | present | present |
| Stalk Length | medium | long | medium | medium |
| Greasiness | present | absent | absent | absent |
| Overcolor Percent | med./high | high | high | high |
| Overcolor | red | red | brownish | brownish |
| Overcolor Type | solid flush and striped | streaked | streaked | solid flush |
| Russet Amount | weak/medium | weak | absent | absent |
| Lenticel Size | small | small | small/med. | medium |
| Flesh Color | greenish | white | cream | greenish |
| Flesh Texture | medium | fine | medium | medium |
| Distinctness of Core-Line | medium | weak | strong | strong |
| Time of Ripeness | late[1] | medium[2] | late[3] | late[3] |

NOTES:
1. 7 days before Granny Smith; 21 days after Red Delicious
2.14 days before Granny Smith; 7–14 days after Red Delicious
3. Golden Delicious Besides its coloration, the size and shape of the Lochbuie Red Braeburn fruit also provides for its distinctiveness (Table 1). Lochbuie Red Braeburn produces a medium to large size fruit which is long and truncated in shape, lacks ribbing and possesses a medium size crown at its distal end. Like the Joburn and Mariri Red varieties, and unlike the Hidala fruit, the Lochbuie Red Braeburn fruit is also asymmetrical in shape (Table 1). The Hidala fruit differs substantially from the Lochbuie Red Braeburn fruit. The Hidala produces a large fruit which is symmetrical, mildly truncated in shape, lacks ribbing and possesses a very weak crown at its distal end. The size and shape of the Lochbuie Red Braeburn fruit can also be distinguished from that of the Joburn and Mariri Red fruits. The major difference lies within the shape of the fruit. Unlike the Lochbuie Red Braeburn fruit, both the Joburn fruit and the Mariri Red fruit have a distinct ribbing pattern to their unique shapes in addition to crowning at their distal ends. More specifically the Joburn fruit has a flat globose shape while the Mariri Red fruit has a short globose conical shape.

The Joburn and Mariri Red varieties produce fruit that is absent of russet, whereas the Hidala fruit shows a weak russet amount and the Lochbuie Red Braeburn fruit shows a weak to medium russet amount (Table 1). Lochbuie Red Braeburn fruit is further distinguished from that of Joburn and Mariri Red in that Lochbuie Red Braeburn has small lenticels and Joburn and Mariri Red have small to medium or medium sized lenticels (Table 1). The core-line of the Lochbuie Red Braeburn fruit also differs from the other varieties mentioned in the sense that the Lochbuie Red Braeburn fruit possesses a medium core-line, whereas the Hidala fruit exhibits a weak core-line and the Joburn and Mariri Red possess a strong core-line (Table 1).

Sensory assessment shows that the Lochbuie Red Braeburn fruit differs from the varieties mentioned above. All of the varieties possess a smooth texture to their surface, however the Lochbuie Red Braeburn fruit exhibits a greasiness not found in the other three varieties (Table 1). The Lochbuie Red Braeburn fruit also has a greenish flesh color, like the Mariri Red but unlike Hidala which has a white colored flesh and Joburn which has a creamy colored flesh (Table 1). One hour after being cut with a stainless steel knife, Lochbuie Red Braeburn fruit exhibits a medium to strong browning of the flesh, whereas the browning is weak in the Hidala fruit, weak to medium in the Joburn fruit, and medium in the Mariri Red. Lochbuie Red Braeburn fruit is considered to be juicy with a weak sweet taste and a strong acid content, while Hidala is considered juicy with a medium sweet taste and a weak acid content. Joburn and Mariri Red exhibit a medium amount of juiciness as compared to the Cox's Orange Pippin.

In all the varieties mentioned above, the flowering begins early in the season. Lochbuie Red Braeburn flowers differ from the other varieties in that the flower petals overlap each other. The petals from Joburn and Mariri Red range from touching to being free from one another, while the Hidala petals are touching but not overlapping. Unlike Joburn and Mariri Red whose dormant one year old shoots have a strong pubescence, the Lochbuie Red Braeburn's dormant one year old shoots have a medium pubescence while the Hidala's shoots have a weak pubescence. The leaf of the Lochbuie Red Braeburn tree also differs from that of the other varieties. The Lochbuie Red Braeburn leaf has a wooly and medium pubescence on its lower side, whereas the Joburn and Mariri Red varieties have a strong pubescence and Hidala has a weak pubescence.

Overall Lochbuie Red Braeburn looks very different to Braeburn, Hidala and Joburn due to the extent and pattern of the red over color of the fruit. Likewise, Lochbuie Red Braeburn can be easily differentiated from Mariri Red due to Mariri Red's darker fruit coloration.

Its distinctive characteristics throughout the tree further distinguishes it from the Braeburn parent variety and its siblings mentioned above.

The following description is of Lochbuie Red Braeburn trees planted in Hawkes Bay, New Zealand, in 1992 on MM106 rootstock. Observations on trees and fruit were made in Autumn 1996. Color measurements were made using The Royal Horticultural Society Colour Charts (R.H.S.C.C.).

Trunk: Medium stockiness, smooth.

Tree: Medium vigor, spreading habit, predominance of bearing on spurs.

Branches: Medium thick, smooth, multi-branching.

*Color of bark.*—1 year old branches, brown (R.H.S.C.C. 200B). Mature bark, grey (R.H.S.C.C. 201C).

Leaves: Upward pose; medium glossiness of upper side; medium pubescence on lower side, medium petiole length.

*Size.*—Small to medium.

*Length to width ratio (fourth to sixth fully expanded leaf).*—Medium.

*Color.*—Green (R.H.S.C.C. 139A).

Flowers: Early-season flowering, medium size; flat shape, margin of petals touching.

*Color of petals soon after opening.*—Red purple (R.H.S.C.C. 63B).

Fruit:

*Ripening.*—Late Season. Over a 2 week period from the 25th March in Hastings, Hawkes Bay, New Zealand.

*Size.*—Medium to large.

*Shape.*—Globose conical, asymmetric in side view, ribbing present, very weak crowning at distil end.

*Stalk cavity.*—Medium depth with medium width.

*Eye basin.*—Shallow-medium depth, medium width (similar to Golden Delicious).

Stem: Medium thickness (similar to Cox's Orange Pippin), short length. (shorter than Cox's Orange Pippin).

Calyx: Half open. Medium sized. (similar to Cox's Orange Pippin).

Sepals:

*Size.*—Short-medium length.

*Spacing of sepals at base.*—Touching.

Skin: Medium to thick; smooth.

*Bloom of skin.*—Absent.

*Greasiness of skin.*—*Absent.*

*Cracking tendency of skin.*—Absent.

*Ground color.*—Yellow green.

*Over color.*—Red blush (R.H.S.C.C. 185A) with some light striping visible on less colored areas of the fruit. Red coloration covers 80–90% of the skin surface.

*Russet.*—Low to medium amount around stem cavity.

*Lenticels.*—Small to medium size.

Flesh: Juicy, medium firmness, yellow-green color, (R.H.S.C.C. 150D) weak browning of flesh (one hour after cutting with stainless steel knife).

*Texture.*—Medium (as for Cox's Orange Pippin).

*Flavour.*—Sweet with mild levels of acidity evident. Mild aroma.

Core:

*Distinctness of core line in cross section (median through locules).*—Medium to strong.

*Aperture of locules in cross section.*—Closed.

Seeds: Medium sized; brown (R.H.S.C.C. 175B).

Use: Dessert.

Keeping quality: Excellent, 4–5 months in coolstorage.

Susceptibility to:

*Insects.*—Susceptible to major insect pests of apple.

*Diseases.*—Susceptible to major bacterial and fungal diseases of apple.

I claim:

1. A new and distinct variety of apple tree substantially as herein shown and described, and characterized particularly as being a sport of 'Braeburn' with bright red fruit coloration which extends over 80% to 90% of the fruit surface.

* * * * *